(12) United States Patent
Mazitschek et al.

(10) Patent No.: US 9,884,850 B2
(45) Date of Patent: Feb. 6, 2018

(54) PYRIMIDINE HYDROXY AMIDE COMPOUNDS AS HDAC6 SELECTIVE INHIBITORS

(71) Applicant: Acetylon Pharmaceuticals, Inc., Boston, MA (US)

(72) Inventors: Ralph Mazitschek, Belmont, MA (US); John H. van Duzer, Georgetown, MA (US)

(73) Assignee: ACETYLON PHARMACEUTICALS, INC., Boston, MA (US)

( * ) Notice: Subject to any disclaimer, the term of this patent is extended or adjusted under 35 U.S.C. 154(b) by 0 days.

(21) Appl. No.: 15/260,855

(22) Filed: Sep. 9, 2016

(65) Prior Publication Data

US 2017/0096413 A1  Apr. 6, 2017

Related U.S. Application Data

(63) Continuation of application No. 14/631,971, filed on Feb. 26, 2015, now Pat. No. 9,464,073.

(60) Provisional application No. 61/944,766, filed on Feb. 26, 2014.

(51) Int. Cl.
    *C07D 239/42* (2006.01)
    *A61K 31/505* (2006.01)
    *C07D 405/12* (2006.01)

(52) U.S. Cl.
    CPC .......... *C07D 405/12* (2013.01); *A61K 31/505* (2013.01); *C07D 239/42* (2013.01)

(58) Field of Classification Search
    CPC ............................ C07D 239/42; A61K 31/505
    USPC .................................. 544/330, 332; 514/275
    See application file for complete search history.

(56) References Cited

U.S. PATENT DOCUMENTS

| | | | |
|---|---|---|---|
| 3,549,633 A | 12/1970 | Grabowski et al. | |
| 6,777,217 B1 | 8/2004 | Schreiber et al. | |
| 7,244,853 B2 | 7/2007 | Schreiber et al. | |
| 7,250,504 B2 | 7/2007 | Grozinger et al. | |
| 7,994,362 B2 | 8/2011 | Schreiber et al. | |
| 8,148,526 B1 | 4/2012 | van Duzer et al. | |
| 8,614,223 B2 | 12/2013 | Van Duzer | |
| 9,278,963 B2 | 3/2016 | van Duzer | |
| 9,403,779 B2 | 8/2016 | Tamang | |
| 9,409,890 B2 | 8/2016 | van Duzer | |
| 9,464,073 B2 | 10/2016 | Mazitschek | |
| 2004/0266769 A1 | 12/2004 | Bressi et al. | |
| 2006/0239909 A1 | 10/2006 | Anderson et al. | |
| 2007/0093413 A1 | 4/2007 | Schreiber et al. | |
| 2007/0149495 A1 | 6/2007 | Bressi et al. | |
| 2008/0207590 A1 | 8/2008 | Deziel et al. | |
| 2009/0023786 A1 | 1/2009 | Miller et al. | |
| 2009/0209590 A1 | 8/2009 | Mazitschek et al. | |
| 2009/0305384 A1 | 12/2009 | Grozinger et al. | |
| 2009/0312363 A1 | 12/2009 | Bradner et al. | |
| 2010/0137196 A1 | 6/2010 | Schreiber et al. | |
| 2011/0218154 A1 | 9/2011 | Schreiber et al. | |
| 2011/0300134 A1 | 12/2011 | van Duzer et al. | |
| 2012/0121502 A1 | 5/2012 | van Duzer et al. | |
| 2013/0225543 A1 | 8/2013 | Jones | |
| 2014/0142104 A1 | 5/2014 | van Duzer et al. | |
| 2014/0357512 A1 | 12/2014 | Jones | |
| 2015/0099744 A1 | 4/2015 | Yang et al. | |
| 2015/0105358 A1 | 4/2015 | Quayle | |
| 2015/0105383 A1 | 4/2015 | Quayle | |
| 2015/0105409 A1 | 4/2015 | Quayle | |
| 2015/0119413 A1 | 4/2015 | Gradilone et al. | |
| 2015/0150871 A1 | 6/2015 | Quayle | |
| 2015/0176076 A1 | 6/2015 | Yang | |
| 2015/0239869 A1 | 8/2015 | Mazitschek et al. | |
| 2015/0250786 A1 | 9/2015 | Berton et al. | |
| 2015/0359794 A1 | 12/2015 | Benz et al. | |
| 2016/0030458 A1 | 2/2016 | Jones | |
| 2016/0158231 A1 | 6/2016 | Jarpe | |
| 2016/0158232 A1 | 6/2016 | Pozzi et al. | |
| 2016/0228434 A1 | 8/2016 | Reilly | |
| 2016/0279128 A1 | 9/2016 | van Duzer | |

FOREIGN PATENT DOCUMENTS

| | | |
|---|---|---|
| EP | 2524918 A1 | 11/2012 |
| WO | 2003/037869 A1 | 5/2003 |
| WO | 2003/076401 A1 | 9/2003 |
| WO | 2003/076430 A1 | 9/2003 |
| WO | 2004/052869 A1 | 6/2004 |
| WO | 2005/012261 A1 | 2/2005 |
| WO | 2005/030705 A1 | 4/2005 |
| WO | 2006/102557 A2 | 9/2006 |
| WO | 2006/123121 A1 | 11/2006 |
| WO | 2007/022638 A1 | 3/2007 |
| WO | 2007/091703 A1 | 8/2007 |
| WO | 2007/130429 A2 | 11/2007 |
| WO | 2008/055068 A2 | 5/2008 |
| WO | 2008/091349 A1 | 7/2008 |
| WO | 2009/137462 A2 | 11/2009 |
| WO | 2010/009155 A2 | 1/2010 |
| WO | 2010/011296 A2 | 1/2010 |
| WO | 2010/080996 A1 | 7/2010 |
| WO | 2011/011186 A1 | 1/2011 |
| WO | 2011/019393 A2 | 2/2011 |
| WO | 2011/084991 A2 | 7/2011 |

OTHER PUBLICATIONS

Pyrimidine Hydroxy Amide Compounds as Protein Deacetylase Inhibitors and Methods of Use Thereof.
Histone Deacetylase (HDAC) Biomarkers in Multiple Myeloma.
Combinations of Histone Deacetylase Inhibitors and Immunomodulatory Drugs.
Combinations of Histone Deacetylase Inhibitors and Either HER2 Inhibitors or PI3K Inhibitors.

(Continued)

*Primary Examiner* — Deepak Rao
(74) *Attorney, Agent, or Firm* — Lathrop Gage LLP; Brian C. Trinque

(57) ABSTRACT

The present invention relates to pyrimidine hydroxy amide compounds, the use of such compounds in the inhibition of HDAC6, and the use of such compounds in the treatment of various diseases, disorders, or conditions related to HDAC6.

9 Claims, 4 Drawing Sheets

(56) References Cited

OTHER PUBLICATIONS

HDAC Inhibitors, Alone or in Comination with PI3K Inhibitors, For Treating Non-Hodgkin's Lymphoma.
Pyrimidine Hydroxy Amide Compounds as Histone Deacetylase Inhibitors.
Treatment of Diseases Caused by Abnormal Lymphocyte Function With an HDAC6 Inhibitor.
Pyrimidine Hydroxy Amide Compounds as HDAC6 Selective Inhibitors.
Histone Deactylase 6 (HDAC6) Biomarkers in Multiple Myeloma.
Pyrimidine Hydroxy Amide Compounds for Treating Peripheral Neuropathy.
Treatment of Leukemia With HDAC Inhibitors.
Histone Deacetylase 6 Selective Inhibitors for the Treatment of Cisplatin-Induced Peripheral Neuropathy.
U.S. Appl. No. 15/170,335, filed Jun. 1, 2016, Matthew B. Jarpe.
Angibaud et al. (2005) "Discovery of Pyrimidyl-5-hydroxamic acids as New Potent Histone Deacetylase Inhibitors," European Journal of Medicinal Chemistry. 40(6):597-606.
Berge et al. (1977) "Pharmaceutical salts," Journal of Pharmaceutical Sciences. 66:1-19.
Butler et al. (2000) "Suberoylanilide Hydroxamic Acid, an Inhibitor of Histone Deactetylase, Suppresses the Growth of Prostate Cancer Cells in Vitro and in Vivo," Cancer Research. 60:5165-5170.
Damasio (1996) "Alzheimer's Disease and Related Dementias," In; Cecil Textbook of Medicine. 20th Ed. vol. 2. pp. 1992-1996.
Foks et al. (1972) "Investigations on Pyrazine Derivatives Part II. Synthesis and Tuberculostatic Action of Some 6 Alkylaminopyrazine-2-carboxylic acids," Dissertationes Pharmaceuticae and Pharmacologicae. 24:(6)577-583.
Foks et al. (1974) "Studies on Pyrazine Derivatives," Pol. J. Pharmacol. Pharm. 26:537-543.
Gennaro: Ed. (1970) Remington's Pharmaceutical Science. 17th Ed. Mack Publishing Co. Easton, Pennsylvania. p. 1418.
Glaser (2007) "HDAC inhibitors: clinical update and mechanism-based potential," Biochem. Pharmacol. 74(5):659-671.
Grozinger et al. (1999) "Three proteins define a class of human histone deacetylases related to yeast Hda1p," Proc. Natl. Acad. Sci. USA. 96:4868-4873.
Gura (1997) "Systems for identifying new drugs are often faulty," Science. 278(5340):1041-1042.
Haggarty et al. (2003) "Domain-selective Small-molecule Inhibitor of Histone Deacetylase 6 (HDAC6)-mediated Tubulin Deacetylation," Proc. Natl. Acad. Sci. USA. 100(8):4389-4394.
Hassig et al. (1997) "Nuclear histone acetylases and deacetylases and transcriptional regulation: HATs off to HDACs," Curr. Opin. Chem. Biol. 1:300-308.
Hu et al. (2000) "Cloning and characterization of a novel human class I histone deacetylase that functions as a transcription repressor," J. Biol. Chem. 275:15254-15264.

Johnson et al. (2001) "Relationships between drug activity in NCI preclinical in vitro and in vivo models and early clinical trials," Br. J. Cancer. 64(10):1424-1431.
Johnstone et al. (2002) "Histone-deacetylase inhibitors: novel drugs for the treatment of cancer," Nature Reviews in Drug Discovery. 1:287-299.
Kao et al. (2000) "Isolation of a novel histone deacetylase reveals that class I and class II deacetylases promote SMRT-mediated repression," Genes Dev. 14:55-66.
Langley et al. (2005) "Remodeling Chromatin and Stress Resistance in the Central Nervous System: Histone Deacetylase Inhibitors as Novel and Broadly Effective Neuroprotective Agents," Current Drug Targets—CNS & Neurological Disorders. 4:41-50.
Layzer (1996) "Degenerative Diseases of the Nervous System," In; Cecil Textbook of Medicine. 20th Ed. vol. 2. pp. 2050-2057.
Marks et al. (2001) "Histone deacetylases and cancer: causes and therapies," Nat. Rev. Cancer. 1:194-202.
Pearce et al. (2008) "Failure Modes in Anticancer Drug Discovery and Development," Ch. 18 In; Cancer Drug Design and Discovery. Ed.: Neidle. pp. 424-435.
Rajak et al. (2011) "2,5-Disubstituted-1,3,4-oxadiazoles/thiadiazole as Surface Recognition Moiety: Design and Synthesis of Novel Hydroxamic acid Based Histone Deacetylase Inhibitors," Bioorganic & Medicinal Chemistry Letters. 21(19):5735-5738.
Simone (1996) "Oncology: Introduction," In; Cecil Textbook of Medicine. 20th Ed. vol. 1. pp. 1004-1010.
Taunton et al. (1996) "A mammalian histone deacetylase related to the yeast transcriptional regulator Rpd3p," Science. 272:408-411.
Venter et al. (2001) "The sequence of the human genome," Science. 291:1304-1351.
Warrell et al. (1998) "Therapeutic targeting of transcription in acute promyelocytic leukemia by use of an inhibitor of histone deacetylase," J. Natl. Cancer Inst. 90:1621-1625.
Yang et al. (1997) "Isolation and characterization of cDNAs corresponding to an additional member of the human histone deacetylase gene family," J. Biol. Chem. 272:28001-28007.
Zhou et al. (2001) "Cloning and characterization of a histone deacetylase, HDAC9," Proc. Natl. Acad. Sci. USA. 98:10572-10577.
International Preliminary Report on Patentability corresponding to International Patent Application No. PCT/US2011/021982, dated Jul. 24, 2012.
International Preliminary Report on Patentability corresponding to International Patent Application No. PCT/US2011/060791, dated May 21, 2013.
International Search Report with Written Opinion corresponding to International Patent Application No. PCT/US2011/021982, dated Oct. 10, 2011.
International Search Report with Written Opinion corresponding to International Patent Application No. PCT/US2011/060791, dated Jun. 13, 2012.
Office Action corresponding to United States Patent Application No. 14/082,472, dated Dec. 30, 2015.
Supplementary European Search Report for Application No. PCT/US2011060791, dated Feb. 25, 2014. 16 pages.

PYRIMIDINE HYDROXY AMIDE COMPOUNDS AS HDAC6 SELECTIVE INHIBITORS

PRIORITY BENEFIT

This application is a continuation of U.S. application Ser. No. 14/631,971, filed Feb. 26, 2015, which claims the benefit of U.S. Provisional Application Ser. No. 61/944,766, filed Feb. 26, 2014, the contents of which are incorporated herein in their entirety.

BACKGROUND

One biological target of recent interest is histone deacetylase (HDAC) (see, for example, a discussion of the use of inhibitors of histone deacetylases for the treatment of cancer: Marks et al. Nature Reviews Cancer 2001, 7,194; Johnstone et al. Nature Reviews Drug Discovery 2002, 287). Post-translational modification of proteins through acetylation and deacetylation of lysine residues plays a critical role in regulating their cellular functions. HDACs are zinc hydrolases that modulate gene expression through deacetylation of the N-acetyl-lysine residues of histone proteins and other transcriptional regulators (Hassig et al Curr. Opin. Chem. Biol. 1997, 1, 300-308). HDACs participate in cellular pathways that control cell shape and differentiation, and an HDAC inhibitor has been shown effective in treating an otherwise recalcitrant cancer (Warrell et al J. Natl. Cancer Inst. 1998, 90, 1621-1625). At this time, eleven human HDACs, which use Zn as a cofactor, have been identified (Taunton et al. Science 1996, 272, 408-411; Yang et al. J. Biol. Chem. 1997, 272, 28001-28007. Grozinger et al. Proc. Natl. Acad. Sci. U.S.A. 1999, 96, 4868-4873; Kao et al. Genes Dev. 2000, 14, 55-66. Hu et al J. Biol. Chem. 2000, 275, 15254-15264; Zhou et al. Proc. Natl. Acad. Sci. U.S.A. 2001, 98, 10572-10577; Venter et al. Science 2001, 291, 1304-1351), and these members fall into three classes (class I, II, and IV). An additional seven HDACs have been identified which use NAD as a cofactor.

Recently, a cytoplasmic histone deacetylase protein, HDAC6, was identified as necessary for aggresome formation and for survival of cells following ubiquitinated misfolded protein stress. The aggresome is an integral component of survival in cancer cells. The mechanism of HDAC6-mediated aggresome formation is a consequence of the catalytic activity of the carboxy-terminal deacetylase domain, targeting an uncharacterized non-histone target. HDAC inhibition results in hyperacetylation of chromatin, alterations in transcription, growth arrest, and apoptosis in cancer cell lines. Early phase clinical trials with available nonselective HDAC inhibitors demonstrate responses in hematologic malignancies including multiple myeloma, although with significant toxicity.

There remains a need for the development of inhibitors of histone deacetylases and tubulin histone deacetylases.

SUMMARY OF THE INVENTION

Provided herein are small molecule inhibitors of HDAC6. In certain embodiments, these compounds are potent and selective inhibitors of HDAC6. The present invention provides compounds, pharmaceutical compositions thereof, and methods of using these compounds to treat disorders related to HDAC6 including cancers, inflammatory disorders, autoimmune disorders, neurological disorders, and neurodegenerative disorders.

In one aspect, provided herein are compounds useful for the treatment of diseases mediated by HDAC6 in a subject in need thereof.

Provided herein are compounds of Formula I:

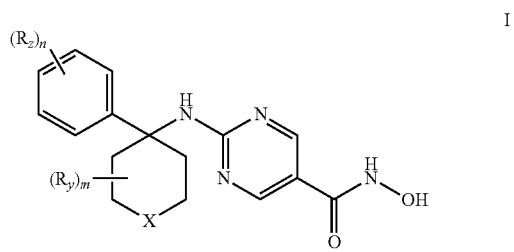

or a pharmaceutically acceptable salt thereof.
In one embodiment, the compound of the invention is

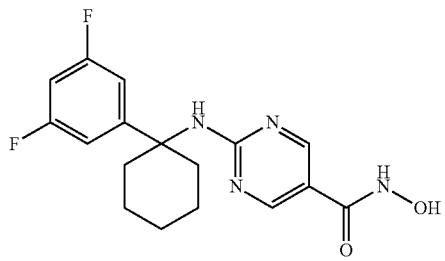 [SMILES: O=C(NO)c1cnc(NC2(c3cc(F)cc(F)c3)CCCCC2)nc1]

or a pharmaceutically acceptable salt thereof.
In another embodiment, the compound of the invention is

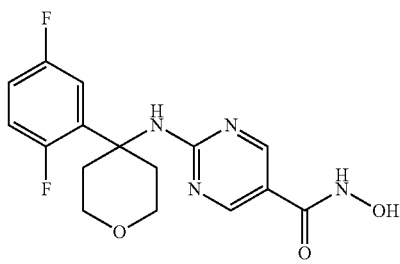 [SMILES: O=C(NO)c1cnc(NC2(c3cc(F)ccc3F)CCOCC2)nc1]

or a pharmaceutically acceptable salt thereof.
In another embodiment, the compound of the invention is

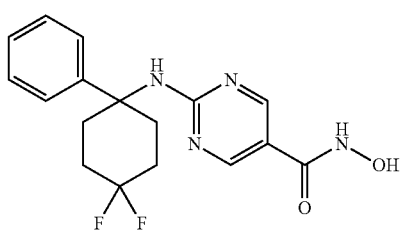 [SMILES: O=C(NO)c1cnc(NC2(c3ccccc3)CCC(F)(F)CC2)nc1]

or a pharmaceutically acceptable salt thereof.

In another embodiment, the compound of the invention is

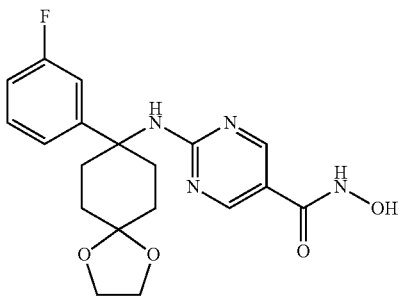 [SMILES: O=C(NO)c1cnc(NC2(c3cccc(F)c3)CCC3(CC2)OCCO3)nc1]

or a pharmaceutically acceptable salt thereof.

In a further aspect, provided herein are pharmaceutical compositions comprising a compound of the invention, or a pharmaceutically acceptable salt thereof, together with a pharmaceutically acceptable carrier.

In one aspect, provided herein is a method of inhibiting the activity of HDAC6 in a subject in need thereof comprising administering to the subject a compound of the invention or a pharmaceutically acceptable salt thereof.

In another aspect, provided herein is a method of selectively inhibiting the activity of HDAC6 over other HDACs in a subject in need thereof comprising administering to the subject a compound of the invention or a pharmaceutically acceptable salt thereof.

In an embodiment, the compound of the invention has a selectivity for HDAC6 when tested in a HDAC enzyme assay of about 5 to 1000 fold greater than for other HDACs.

In another aspect, provided herein is a method of treating a disease mediated by HDAC6 in a subject in need thereof comprising administering to the subject a compound of the invention, or a pharmaceutically acceptable salt thereof, or a pharmaceutical composition comprising a compound of the invention.

In one embodiment, the disease to be treated by the methods of the invention is a cancer or a proliferation disease.

In a further embodiment, the cancer is selected from the group consisting of lung cancer, colon cancer, breast cancer, prostate cancer, liver cancer, brain cancer, kidney cancer, ovarian cancer, stomach cancer, skin cancer, bone cancer, gastric cancer, pancreatic cancer, glioma, glioblastoma, hepatocellular carcinoma, papillary renal carcinoma, head and neck squamous cell carcinoma, leukemias, lymphomas, and myelomas.

In another embodiment, the cancer is a solid tumor. In a further embodiment, the solid tumor is lung cancer, colon cancer, breast cancer, prostate cancer, liver cancer, brain cancer, kidney cancer, ovarian cancer, stomach cancer, skin cancer, bone cancer, gastric cancer, pancreatic cancer, glioma, glioblastoma, hepatocellular carcinoma, papillary renal carcinoma, head and neck squamous cell carcinoma.

In a preferred embodiment, the cancer is multiple myeloma.

In another embodiment, the disease to be treated by the methods provided herein is Wilson's disease, spinocerebellar ataxia, prion disease, Parkinson's disease, Huntington's disease, amytrophic lateral sclerosis, amyloidosis, Alzheimer's disease, Alexander's disease, alcoholic liver disease, cystic fibrosis, Pick's Disease, spinal muscular dystrophy, Lewy body dementia or chemotherapy-induced cognitive dysfunction.

In yet another embodiment, the disease is rheumatoid arthritis, osteoarthritis, rheumatoid spondylitis, psoriasis, post ischemic perfusion injury, inflammatory bowel disease, chronic inflammatory pulmonary disease, eczema, asthma, psoriasis, ischemia/reperfusion injury, ulcerative colitis, acute respiratory distress syndrome, psoriatic arthritis, infectious arthritis, progressive chronic arthritis, deforming arthritis, osteoarthritis, traumatic arthritis, gouty arthritis, Reiter's syndrome, polychondritis, acute synovitis and spondylitis, glomerulonephritis, hemolytic anemia, aplasic anemia, idiopathic thrombocytopenia, neutropenia, ulcerative colitis, Crohn's disease, host versus graft disease, graft versus host disease, allograft rejection, chronic thyroiditis, Graves' disease, scleroderma, diabetes, active hepatitis, primary binary cirrhosis, myasthenia gravis, multiple sclerosis (MS), systemic lupus erythematosus, atopic dermatitis, contact dermatitis, skin sunburns, chronic renal insufficiency, Stevens-Johnson syndrome, idiopathic sprue, sarcoidosis, Guillain-Barre syndrome, uveitis, conjunctivitis, keratoconjunctivitis, otitis media, periodontal disease, pulmonary interstitial fibrosis, asthma, bronchitis, rhinitis, sinusitis, pneumoconiosis, pulmonary insufficiency syndrome, pulmonary emphysema, pulmonary fibrosis, silicosis, autosomal dominant polycystic kidney disease, autosomal recessive polycystic kidney disease, Alstrom syndrome, Bardet-Biedl syndrome, Joubert syndrome, Meckel-Gruber syndrome, nephronophthisis, orofaciodigital syndrome 1, Senior-Loken syndrome, or primary ciliary dyskinesia (Kartagener Syndrome).

In an aspect, provided herein is a method of treating a subject suffering from or susceptible to multiple myeloma comprising administering to a subject in need thereof a therapeutically effective amount of a compound of the invention, or a pharmaceutical composition comprising the compound of the invention, to thereby treat the subject suffering from or susceptible to multiple myeloma.

In an aspect, provided herein are methods of treating or preventing a peripheral neuropathy in a subject in need thereof comprising administering to the subject a therapeutically effective amount of a compound of the invention, or a pharmaceutical composition comprising the compound of the invention, to thereby treat or prevent the peripheral neuropathy in the subject.

In an embodiment, the peripheral neuropathy is Charcot-Marie Tooth Disease.

In another embodiment, the peripheral neuropathy is chemotherapy induced peripheral neuropathy. In yet a further embodiment, the chemotherapy induced peripheral neuropathy is taxol induced peripheral neuropathy or vincristine induced peripheral neuropathy. In a preferred embodiment, the chemotherapy induced peripheral neuropathy is taxol induced peripheral neuropathy.

In an embodiment of any of the method of the invention, the subject is a human.

In another aspect, provided herein is a method of treating a subject suffering from or susceptible to multiple myeloma comprising administering to a subject in need thereof a therapeutically effective amount of the compound:

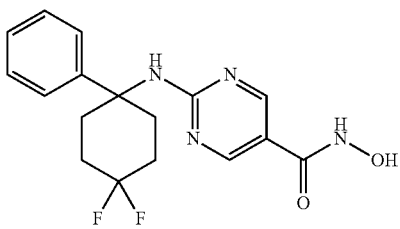 [SMILES: O=C(NO)c1cnc(NC2(c3ccccc3)CCC(F)(F)CC2)nc1]

or a pharmaceutically acceptable salt thereof, to thereby treat the subject suffering from or susceptible to multiple myeloma.

In another aspect, provided herein is a method of treating or preventing a peripheral neuropathy in a subject in need thereof comprising administering to the subject a therapeutically effective amount of the compound:

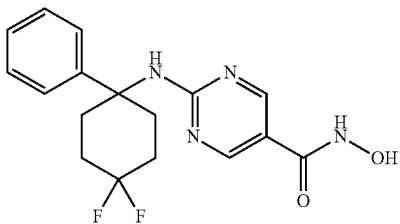 [SMILES: O=C(NO)c1cnc(NC2(c3ccccc3)CCC(F)(F)CC2)nc1]

or a pharmaceutically acceptable salt thereof, to thereby to thereby treat or prevent the peripheral neuropathy in the subject.

In an embodiment, the peripheral neuropathy is Charcot-Marie Tooth Disease.

In another embodiment, the peripheral neuropathy is chemotherapy induced peripheral neuropathy. In yet a further embodiment, the chemotherapy induced peripheral neuropathy is taxol induced peripheral neuropathy or vincristine induced peripheral neuropathy. In a preferred embodiment, the chemotherapy induced peripheral neuropathy is taxol induced peripheral neuropathy

DETAILED DESCRIPTION

Definitions

Figure 1:
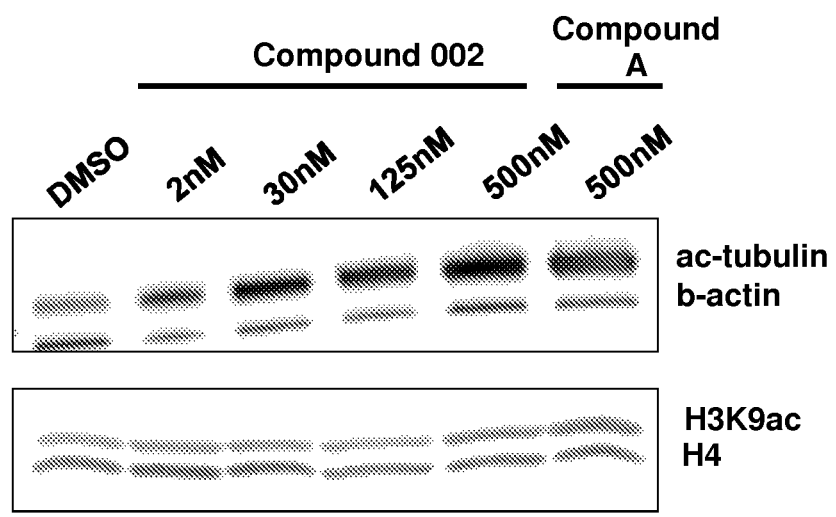
FIG. 1 shows tubulin and histone acetylation of SH-SY5Y neuroblastoma cells after 5 h of treatment with various concentrations of Compound 002 and 500 nM of Compound A.

Listed below are definitions of various terms used to describe this invention. These definitions apply to the terms as they are used throughout this specification and claims, unless otherwise limited in specific instances, either individually or as part of a larger group.

The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "about" generally indicates a possible variation of no more than 10%, 5%, or 1% of a value. For example, "about 25 mg/kg" will generally indicate, in its broadest sense, a value of 22.5-27.5 mg/kg, i.e., 25±2.5 mg/kg.

The term "alkyl" refers to saturated, straight- or branched-chain hydrocarbon moieties containing, in certain embodiments, between one and six, or one and eight carbon atoms, respectively. Examples of $C_{1-6}$-alkyl moieties include, but are not limited to, methyl, ethyl, propyl, isopropyl, n-butyl, tert-butyl, neopentyl, n-hexyl moieties; and examples of $C_{1-8}$-alkyl moieties include, but are not limited to, methyl, ethyl, propyl, isopropyl, n-butyl, tert-butyl, neopentyl, n-hexyl, heptyl, and octyl moieties.

The term "alkoxy" refers to an —O-alkyl moiety.

The term "aryl" refers to a mono- or poly-cyclic carbocyclic ring system having one or more aromatic rings, fused or non-fused, including, but not limited to, phenyl, naphthyl, tetrahydronaphthyl, indanyl, idenyl, and the like. In some embodiments, aryl groups have 6 carbon atoms. In some embodiments, aryl groups have from six to ten carbon atoms. In some embodiments, aryl groups have from six to sixteen carbon atoms.

The term "cycloalkyl" denotes a monovalent group derived from a monocyclic or polycyclic saturated or partially unsaturated carbocyclic ring compound. Examples of $C_{3-8}$-cycloalkyl include, but are not limited to, cyclopropyl, cyclobutyl, cyclopentyl, cyclohexyl, cycloheptyl and cyclooctyl; and examples of $C_{3-12}$-cycloalkyl include, but are not limited to, cyclopropyl, cyclobutyl, cyclopentyl, cyclohexyl, bicyclo [2.2.1] heptyl, and bicyclo [2.2.2] octyl. Also contemplated are monovalent groups derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl" refers to a mono- or poly-cyclic (e.g., bi-, or tri-cyclic or more) fused or non-fused moiety or ring system having at least one aromatic ring, where one or more of the ring-forming atoms is a heteroatom such as oxygen, sulfur, or nitrogen. In some embodiments, the heteroaryl group has from about one to six carbon atoms, and in further embodiments from one to fifteen carbon atoms. In some embodiments, the heteroaryl group contains five to sixteen ring atoms of which one ring atom is selected from oxygen, sulfur, and nitrogen; zero, one, two, or three ring atoms are additional heteroatoms independently selected from oxygen, sulfur, and nitrogen; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiazolyl, thiadiazolyl, oxadiazolyl, thiophenyl, furanyl, indolyl, quinolinyl, isoquinolinyl, benzimidazolyl, benzooxazolyl, quinoxalinyl, acridinyl, and the like.

The term "heterocycloalkyl" refers to a non-aromatic 3-, 4-, 5-, 6- or 7-membered ring or a bi- or tri-cyclic group fused of non-fused system, where (i) each ring contains between one and three heteroatoms independently selected from oxygen, sulfur, and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

In accordance with the invention, any of the aryls, substituted aryls, heteroaryls and substituted heteroaryls described herein, can be any aromatic group.

The terms "halo" and "halogen" refer to an atom selected from fluorine, chlorine, bromine, and iodine.

The term "HDAC" refers to histone deacetylases, which are enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hda1 gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

The term "inhibitor" is synonymous with the term antagonist.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Additionally, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17$^{th}$ ed., Mack Publishing Company, Easton, Pa., 1985, p. 1418 and Journal of Pharmaceutical Science, 66, 2 (1977), each of which is incorporated herein by reference in its entirety.

Combinations of substituents and variables envisioned by this invention are only those that result in the formation of stable compounds. The term "stable" refers to compounds which possess stability sufficient to allow manufacture and which maintains the integrity of the compound for a sufficient period of time to be useful for the purposes detailed herein (e.g., therapeutic or prophylactic administration to a subject).

The term "subject" refers to a mammal. A subject therefore refers to, for example, dogs, cats, horses, cows, pigs, guinea pigs, and the like. Preferably the subject is a human. When the subject is a human, the subject may be referred to herein as a patient.

The terms "treat," "treating," and "treatment" refer to a method of alleviating or abating a disease and/or its attendant symptoms.

The terms "prevent," "preventing," and "prevention" refer to administration of the compound of the invention, or a pharmaceutical composition thereof in order to prevent a disease, condition, or disorder in an individual who may be predisposed or likely to exhibit said disease, condition, or disorder, but does not yet experience or exhibit the pathology or symptomatology of the disease, condition, or disorder.

Compounds of the Invention

In one aspect, provided herein is a compound of Formula I:

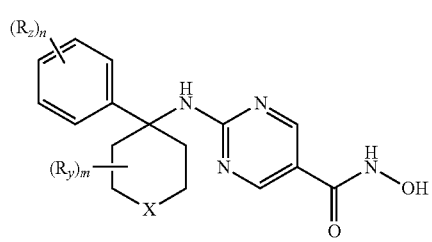

or a pharmaceutically acceptable salt thereof,
wherein,
X is C or O;
$R_y$ is independently, at each occurrence, selected from the group consisting of $C_{1-6}$-alkyl, $C_{1-6}$-alkoxy, halo, —$C_{1-6}$ haloalkyl, —$C_{1-6}$ dihaloalkyl, —$C_{1-6}$ trihaloalkyl, —OH, —N(R$^1$)$_2$, —C(O)R$^1$, —CO$_2$R$^1$, and —C(O)N(R$^1$)$_2$;
or:
two $R_y$ groups on the same or adjacent carbon atoms are taken together to form a $C_{3-8}$-cycloalkyl or $C_{3-7}$-heterocycloalkyl ring, each of which may be fused or isolated;
$R_z$ is independently, at each occurrence, selected from the group consisting of $C_{1-6}$-alkyl, $C_{1-6}$-alkoxy, halo, —$C_{1-6}$ haloalkyl, —$C_{1-6}$ dihaloalkyl, —$C_{1-6}$ trihaloalkyl, —OH, —N(R$^2$)$_2$, —C(O)R$^2$, —CO$_2$R$^2$, —C(O)N(R$^2$)$_2$;
each R$^1$ is independently, at each occurrence, selected from the group consisting of H, $C_{1-6}$-alkyl, $C_{3-8}$-cycloalkyl, $C_{3-7}$-heterocycloalkyl, aryl, heteroaryl, $C_{1-6}$-alkyl-cycloalkyl, $C_{1-6}$-alkyl-heterocycloalkyl, $C_{1-6}$-alkyl-aryl, and $C_{1-6}$-alkyl-heteroaryl;
each R$^2$ is independently, at each occurrence, selected from the group consisting of H or $C_{1-6}$-alkyl;
m is 0, 1, 2, or 3; and
n is 0, 1, 2, or 3.

In an embodiment of the compounds of Formula I, n is 1 or 2 and $R_z$ is halo.

In another embodiment of the compounds of Formula I, X is C and m is 1 or 2. In a preferred embodiment, X is C, m is 1 or 2, and $R_y$ is halo or $C_{1-6}$-alkoxy. In another embodiment, two $R_y$ groups on the same or adjacent carbon atoms are taken together to form a $C_{3-8}$-cycloalkyl or $C_{3-7}$-heterocycloalkyl ring and $R_y$ is $C_{1-6}$-alkoxy. In a preferred embodiment, two $R_y$ groups on the same carbon atom are taken together to form a $C_{3-8}$-cycloalkyl or $C_{3-7}$-heterocycloalkyl ring.

Preferred embodiments of Formula I, including pharmaceutically acceptable salts thereof, are shown below in Table 1. All compounds of Formula I, as well as pharmaceutically acceptable salts thereof, and the compounds of Table 1, as well as pharmaceutically acceptable salts thereof, are considered to be "compounds of the invention."

TABLE 1

| Compound ID | Structure |
|---|---|
| 001 | 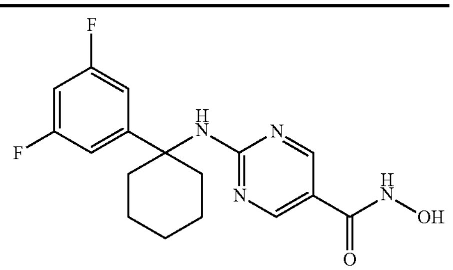 |
| 002 | 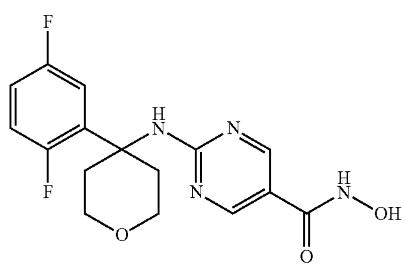 [SMILES: O=C(NO)c1cnc(NC2(c3cc(F)ccc3F)CCOCC2)nc1] |
| 003 | 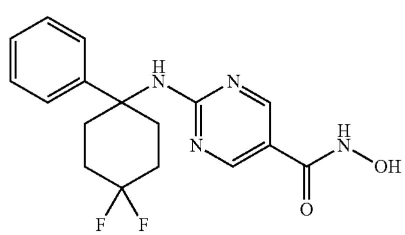 [SMILES: O=C(NO)c1cnc(NC2(c3ccccc3)CCC(F)(F)CC2)nc1] |
| 004 | 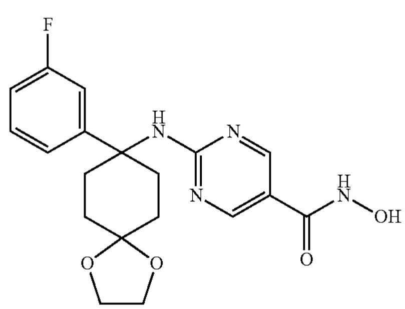 [SMILES: O=C(NO)c1cnc(NC2(c3cccc(F)c3)CCC3(CC2)OCCO3)nc1] |

Another embodiment provided herein is a method of making a compound of any of the formulae herein using any one, or combination of, reactions delineated herein. The method can include the use of one or more intermediates or chemical reagents delineated herein.

Another embodiment is an isotopically labeled compound of any of the formulae delineated herein. Such compounds have one or more isotope atoms which may or may not be radioactive (e.g., $^3H$, $^2H$, $^{14}C$, $^{13}C$, $^{35}S$, $^{32}P$, $^{125}I$, and $^{131}I$) introduced into the compound. Such compounds are useful for drug metabolism studies and diagnostics, as well as therapeutic applications.

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry," 3rd edition, John Wiley and Sons, Inc., 1999, and subsequent editions thereof.

Compounds of the present invention can be prepared or formed as solvates (e.g., hydrates). Hydrates of compounds of the present invention can be prepared by recrystallization from an aqueous/organic solvent mixture, using organic solvents such as dioxane, tetrahydrofuran or methanol.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present invention. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., "Enantiomers, Racemates, and Resolutions" (John Wiley & Sons, 1981). The compounds of this invention may also be represented in multiple tautomeric forms, in such instances, the invention expressly includes all tautomeric forms of the compounds described herein. When the compounds described herein contain olefinic double bonds or other centers of geometric asymmetry, and unless specified otherwise, it is intended that the compounds include both E and Z geometric isomers.

Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present invention. All crystal forms of the compounds described herein are expressly included in the present invention.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired compounds of the present invention. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Methods of the Invention

Histone deacetylase is known to play an essential role in the transcriptional machinery for regulating gene expression, induce histone hyperacetylation and to affect the gene expression. Therefore, it is useful as a therapeutic or prophylactic agent for diseases caused by abnormal gene expression such as, for example, inflammatory disorders, diabetes, diabetic complications, homozygous thalassemia, fibrosis, cirrhosis, acute promyelocytic leukemia (APL), organ transplant rejections, autoimmune diseases, protozoal infections, tumors, etc.

Aberrant histone deacetylase activity has also been linked to various neurological and neurodegenerative disorders, including stroke, Huntington's disease, Amyotrophic Lateral Sclerosis and Alzheimer's disease. HDAC inhibition may induce the expression of anti-mitotic and anti-apoptotic genes, such as p21 and HSP-70, which facilitate survival. HDAC inhibitors can act on other neural cell types in the central nervous system, such as reactive astrocytes and microglia, to reduce inflammation and secondary damage during neuronal injury or disease. HDAC inhibition is a promising therapeutic approach for the treatment of a range of central nervous system disorders (Langley B. et al., 2005, Current Drug Targets—CNS & Neurological Disorders, 4: 41-50).

In one aspect, the invention provides a method of selectively inhibiting HDAC6 over other HDACs (e.g., HDAC1, HDAC2, and HDAC3) in a subject, comprising administering to the subject a compound of Formula I or any of the compounds of Table 1 or pharmaceutically acceptable salts thereof.

In one embodiment, the compound of any of the formulae herein (e.g., formula I) has a selectivity for HDAC6 of 5 to 1000 fold over other HDACs.

In another embodiment, the compound of any of the formulae herein (e.g., formula I) has a selectivity for HDAC6 when tested in a HDAC enzyme assay of about 5 to 1000 fold over other HDACs.

In certain embodiments, the compound has a selectivity for HDAC6 of 15 to 40 fold over other HDACs.

In another aspect, the invention provides a method of treating a disease mediated by HDAC6 in a subject comprising administering to the subject a compound of Formula I any of the compounds of Table 1.

In certain embodiments, the disease is cancer or a proliferation disease.

In a further embodiment, the disease is a cancer selected from lung cancer, colon cancer, breast cancer, prostate cancer, liver cancer, brain cancer, kidney cancer, ovarian cancer, stomach cancer, skin cancer, bone cancer, gastric cancer, pancreatic cancer, glioma, glioblastoma, hepatocellular carcinoma, papillary renal carcinoma, head and neck squamous cell carcinoma, leukemias, lymphomas, and myelomas.

In another embodiment, the cancer is a solid tumor. In a further embodiment, the solid tumor is lung cancer, colon cancer, breast cancer, prostate cancer, liver cancer, brain cancer, kidney cancer, ovarian cancer, stomach cancer, skin cancer, bone cancer, gastric cancer, pancreatic cancer, glioma, glioblastoma, hepatocellular carcinoma, papillary renal carcinoma, head and neck squamous cell carcinoma.

In a further embodiment, the cancer is multiple myeloma.

In other embodiments, the disease is Wilson's disease, spinocerebellar ataxia, prion disease, Parkinson's disease, Huntington's disease, amytrophic lateral sclerosis, amyloidosis, Alzheimer's disease, Alexander's disease, alcoholic liver disease, cystic fibrosis, Pick's Disease, spinal muscular dystrophy, Lewy body dementia or chemotherapy-induced cognitive dysfunction.

In other embodiments, the disease is an inflammatory, immune or autoimmune diseases including, but not limited to, arthritic conditions, such as, rheumatoid arthritis, osteoarthritis, juvenile arthritis, or rheumatoid spondylitis; psoriasis; post ischemic perfusion injury; inflammatory bowel disease; chronic inflammatory pulmonary disease;

eczema; asthma; psoriasis; ischemia/reperfusion injury; ulcerative colitis; acute respiratory distress syndrome; psoriatic arthritis; infectious arthritis; progressive chronic arthritis; deforming arthritis; osteoarthritis; traumatic arthritis; gouty arthritis; Reiter's syndrome; polychondritis; acute synovitis and spondylitis; glomerulonephritis (with or without nephrotic syndrome); autoimmune hematologic disorders (e.g. hemolytic anemia, aplastic anemia, idiopathic thrombocytopenia and neutropenia); ulcerative colitis; Crohn's disease; host versus graft disease; graft versus host disease; allograft rejection; chronic thyroiditis; Graves' disease; schleroderma; diabetes (type I and type II); active hepatitis (acute and chronic); primary binary cirrhosis; myasthenia gravis; multiple sclerosis (MS); systemic lupus erythematosus; atopic dermatitis; contact dermatitis; skin sunburns; chronic renal insufficiency; Stevens-Johnson syndrome; idiopathic sprue; sarcoidosis; Guillain-Barre syndrome; uveitis; conjunctivitis; keratoconjunctivitis; otitis media; periodontal disease; pulmonary interstitial fibrosis; asthma; bronchitis; rhinitis; sinusitis; pneumoconiosis; pulmonary insufficiency syndrome; pulmonary emphysema; pulmonary fibrosis; silicosis; chronic inflammatory pulmonary disease (e.g. chronic obstructive pulmonary disease); and other inflammatory or obstructive diseases of the airways.

In another embodiment, the HDAC6 inhibitors of the invention are useful for treating diseases of or related to the kidney, including but not limited to, autosomal dominant polycystic kidney disease, autosomal recessive polycystic kidney disease, Alstrom syndrome, Bardet-Biedl syndrome, Joubert syndrome, Meckel-Gruber syndrome, nephronophthisis, orofaciodigital syndrome 1, Senior-Loken syndrome, or primary ciliary dyskinesia (Kartagener Syndrome).

In one embodiment, the HDAC6 inhibitors of the invention are useful for treating any one or more of the following autoimmune diseases or disorders: systemic lupus erythematosis, autoimmune thyroiditis, dermatitis (including atopic dermatitis and eczematous dermatitis), psoriasis, including keratoconjunctivitis sicca secondary to Sjögren's Syndrome, alopecia areata, allergic responses due to arthropod bite reactions, aphthous ulcer, iritis, conjunctivitis, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, idiopathic thrombocytopenia, polychondritis, Wegener's granulomatosis, chronic active hepatitis, lichen planus, sarcoidosis, primary biliary cirrhosis, uveitis posterior, and interstitial lung fibrosis.

Additionally, the methods of the invention may also be useful in the treatment of protozoal infections. The methods of the invention are also useful in the treatment of diseases associated with aberrant protein catabolism, for example, protein degradation disorders, disorders associated with misfolded proteins, and protein deposition disorders. In certain embodiments, the HDAC6 inhibitors of the invention are useful in the treatment of the protein deposition disorders, Wilson's disease, spinocerebellar ataxia, prion disease, Parkinson's disease, Huntington's disease, amyotrophic lateral sclerosis, spinal muscular atrophy, spinal and bulbar muscular atrophy, amyloidosis, Alzheimer's disease, Alexander's disease, alcoholic liver disease, cystic fibrosis, Pick's disease, Lewy body dementia and chemotherapy-induced cognitive dysfunction.

Neurodegenerative diseases that can be treated or prevented include Alzheimer's disease, Parkinson's disease, cerebral ischaemia, traumatic neurodegenerative disease, Huntington's disease or chorea, senile dementia, memory disorder, vascular dementia, lesions associated with cerebral ischemia (stroke), and with cranial and medullary trauma, among others.

Preferably, the HDAC6 inhibitors are selective inhibitors of HDAC6 and, as such, are useful in the treatment of disorders modulated by histone deacetylases. In one embodiment, the HDAC6 inhibitors of the invention are selective inhibitors of tubulin deacetylases and, as such, are useful in the treatment of disorders modulated by tubulin deacetylases.

Thus, in another aspect of the invention, methods for the treatment of cancer are provided comprising administering a therapeutically effective amount of an HDAC6 inhibitor, as described herein, to a subject in need thereof. In certain embodiments, the subject is identified as in need of such treatment. In certain embodiments, a method for the treatment of a diseases is provided comprising administering a therapeutically effective amount of an HDAC6 inhibitor, or a pharmaceutical composition comprising an HDAC6 inhibitor to a subject in need thereof, in such amounts and for such time as is necessary to achieve the desired result.

In certain embodiments, the method involves the administration of a therapeutically effective amount of an HDAC6 inhibitor or a pharmaceutically acceptable derivative thereof to a subject (including, but not limited to a human or animal) in need of it (including a subject identified as in need). In certain embodiments, the HDAC6 inhibitors are useful for the treatment of cancer (including, but not limited to, glioblastoma, retinoblastoma, breast cancer, cervical cancer, colon and rectal cancer, leukemia (e.g., CML, AML, CLL, ALL), lymphoma, lung cancer (including, but not limited to small cell lung cancer), melanoma and/or skin cancer, multiple myeloma, non-Hodgkin's lymphoma, ovarian cancer, pancreatic cancer, prostate cancer and gastric cancer, bladder cancer, uterine cancer, kidney cancer, testicular cancer, stomach cancer, brain cancer, liver cancer, or esophageal cancer, melanoma and multiple melanoma). In certain embodiments, the HDAC6 inhibitors of the invention are active against leukemia cells and melanoma cells, and thus are useful for the treatment of leukemias (e.g., myeloid, lymphocytic, myelocytic and lymphoblastic leukemias) and malignant melanomas. In still other embodiments, the inventive anticancer agents are active against solid tumors (e.g., lung cancer, colon cancer, breast cancer, prostate cancer, liver cancer, brain cancer, kidney cancer, ovarian cancer, stomach cancer, skin cancer, bone cancer, gastric cancer, pancreatic cancer, glioma, glioblastoma, hepatocellular carcinoma, papillary renal carcinoma, head and neck squamous cell carcinoma). Accordingly, in yet another aspect, according to the methods of treatment of the present invention, tumor cells are killed, or their growth is inhibited by contacting said tumor cells with an HDAC6 inhibitor, as described herein.

In another aspect, provided herein are methods of treating or preventing a peripheral neuropathy in a subject in need thereof comprising administering to the subject a therapeutically effective amount of a compound of Formula I, or a pharmaceutical composition comprising a compound of Formula I, to thereby treat or prevent the peripheral neuropathy. In an embodiment, the compound of Formula I is a compound of Table 1. In a preferred embodiment, the compound of Formula I is Compound 003.

In an embodiment, the peripheral neuropathy is Charcot-Marie Tooth Disease.

In another embodiment, the peripheral neuropathy is a medication induced neuropathy.

In a further embodiment, the peripheral neuropathy is chemotherapy induced peripheral neuropathy. In yet a further embodiment, the chemotherapy induced peripheral neuropathy is taxol induced peripheral neuropathy or vincristine induced peripheral neuropathy.

The chemotherapy induced peripheral neuropathy may be associated with various classes of chemotherapeutics including, but not limited to, thalidomide and thalidomide derivatives, epithilones, vinca alkaloids, taxanes, proteasome inhibitors, and platinum-based chemotherapeutics.

Specific chemotherapies associated with peripheral neuropathy include, but are not limited to, cisplatin, carboplatin, oxaliplatin, bortezomib, dicarbazine, procarbazine, thalidomide, lenalidomide, pomalidomide, misonidazole, etoposide, altretamine, docetaxel, ixabepilone, streptozocin, syclophosphamide, carmustine, lomustine, procarbazine, mitomyocin, cytarabine, methotrexate, 5-fluorouracil, vinblastine, vincristine, bleomycin, paclitaxel, asparaginase, busulfan, dacarbazine, fludarabine, hydroxyurea, ifosfamide, mercaptopurine, mitotane, streptozocin, taxol or a mixture of two or more agents thereof.

In certain embodiments, the invention provides a method of treatment of any of the disorders described herein, wherein the subject is a human.

In accordance with the foregoing, the present invention further provides a method for preventing or treating any of the diseases or disorders described above in a subject in need of such treatment, which method comprises administering to said subject a therapeutically effective amount of an HDAC6 inhibitor of the invention or a pharmaceutically acceptable salt thereof. For any of the above uses, the required dosage will vary depending on the mode of administration, the particular condition to be treated and the effect desired.

In another aspect, the invention provides a method of treating a subject suffering from or susceptible to multiple myeloma comprising administering to a subject in need thereof a therapeutically effective amount of a compound of Formula I, or any of the compounds of Table 1, or pharmaceutically acceptable salts thereof.

In other embodiments of the methods as described herein, the subject is a human.

As discussed above, the present invention provides compounds useful for the treatment of various diseases. In certain embodiments, the compounds of the present invention are useful as inhibitors of histone or tubulin deacetylases and thus are useful as anti-cancer agents, and thus may be useful in the treatment of cancer, by effecting tumor cell death or inhibiting the growth of tumor cells. In certain exemplary embodiments, the inventive anticancer agents are useful in the treatment of cancers and other proliferative disorders, as described above. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. In certain embodiments, the compounds are useful in the treatment of multiple myeloma.

The compounds of the invention are also effective to treat or prevent autoimmune hematologic disorders (e.g. hemolytic anemia, aplastic anemia, idiopathic thrombocytopenia and neutropenia), chronic inflammatory pulmonary disease (e.g. chronic obstructive pulmonary disease) and other inflammatory or obstructive diseases of the airways.

In exemplary embodiments, the compounds of the invention are useful for disorders associated with histone deacetylation activity. In certain exemplary embodiments, the compounds of the invention are useful for disorders associated with tubulin deacetylation activity.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

As discussed above, the compounds of the invention are selective inhibitors of HDAC6 and, as such, are useful in the treatment of disorders modulated by histone deacetylases. As discussed above, the compounds of the invention are selective inhibitors of tubulin deacetylases and, as such, are useful in the treatment of disorders modulated by tubulin deacetylases. For example, compounds of the invention may be useful in the treatment of cancer (e.g., breast cancer, prostate cancer, multiple myeloma, leukemia, lymphoma, etc.). Accordingly, in yet another aspect, according to the methods of treatment of the present invention, tumor cells are killed, or their growth is inhibited by contacting said tumor cells with an inventive compound or composition, as described herein.

Thus, in another aspect of the invention, methods for the treatment of cancer are provided comprising administering a therapeutically effective amount of an inventive compound (i.e., of any of the formulae herein), as described herein, to a subject in need thereof. In certain embodiments, the subject is identified as in need of such treatment. In certain embodiments, a method for the treatment of cancer is provided comprising administering a therapeutically effective amount of an inventive compound, or a pharmaceutical composition comprising an inventive compound to a subject in need thereof, in such amounts and for such time as is necessary to achieve the desired result. In certain embodiments of the present invention a "therapeutically effective amount" of the inventive compound or pharmaceutical composition is that amount effective for killing or inhibiting the growth of tumor cells. The compounds and compositions, according to the method of the present invention, may be administered using any amount and any route of administration effective for killing or inhibiting the growth of tumor cells. Thus, the expression "amount effective to kill or inhibit the growth of tumor cells," as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like.

In certain embodiments, the method involves the administration of a therapeutically effective amount of the compound or a pharmaceutically acceptable derivative thereof to a subject (including, but not limited to a human or animal) in need of it.

The instant invention provides a method of treating a subject suffering from or susceptible to multiple myeloma comprising administering to a subject in need thereof a therapeutically effective amount of a compound of Formula I or any of the compounds of Table 1 or pharmaceutically acceptable salts thereof.

In certain embodiments, the invention provides a method of treatment of any of the disorders described herein, wherein the subject is a human.

In accordance with the foregoing, the present invention further provides a method for preventing or treating any of the diseases or disorders described above in a subject in need of such treatment, which method comprises administering to said subject a therapeutically effective amount of a compound of the invention or a pharmaceutically acceptable salt thereof. For any of the above uses, the required dosage will vary depending on the mode of administration, the particular condition to be treated and the effect desired.

According to the methods of treatment of the present invention, disorders are treated or prevented in a subject, such as a human or other animal, by administering to the subject a therapeutically effective amount of a compound of the invention, in such amounts and for such time as is necessary to achieve the desired result. The term "therapeutically effective amount" of a compound of the invention means a sufficient amount of the compound so as to decrease the symptoms of a disorder in a subject. As is well understood in the medical arts a therapeutically effective amount of a compound of this invention will be at a reasonable benefit/risk ratio applicable to any medical treatment.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight (0.05 to 4.5 mg/m$^2$). An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

In certain embodiments, a therapeutic amount or dose of the compounds of the present invention may range from about 0.1 mg/kg to about 500 mg/kg (about 0.18 mg/m$^2$ to about 900 mg/m$^2$), alternatively from about 1 to about 50 mg/kg (about 1.8 to about 90 mg/m$^2$). In general, treatment regimens according to the present invention comprise administration to a patient in need of such treatment from about 10 mg to about 1000 mg of the compound(s) of this invention per day in single or multiple doses. Therapeutic amounts or doses will also vary depending on route of administration, as well as the possibility of co-usage with other agents.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Pharmaceutical Compositions

In another aspect, the invention provides a pharmaceutical composition comprising any of the compounds of the instant invention (compounds of Formula I or any one of the compounds of Table 1) or pharmaceutically acceptable salts thereof, together with a pharmaceutically acceptable carrier.

The pharmaceutical compositions of the present invention comprise a therapeutically effective amount of a compound of the present invention formulated together with one or more pharmaceutically acceptable carriers. The term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Compounds of the invention can be administered as pharmaceutical compositions by any conventional route, in particular enterally, for example, orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as a magnesium stearate and microcrystalline cellulose. In the case of capsules, tablets and pills, the dosage forms may also comprise buffering agents.

EXAMPLES

Examples have been set forth below for the purpose of illustration and to describe certain specific embodiments of the invention. However, the scope of the claims is not to be in any way limited by the examples set forth herein. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims. Definitions of the variables in the structures in the schemes herein are commensurate with those of corresponding positions in the formulae presented herein.

Example 1

Synthesis of Compound 001

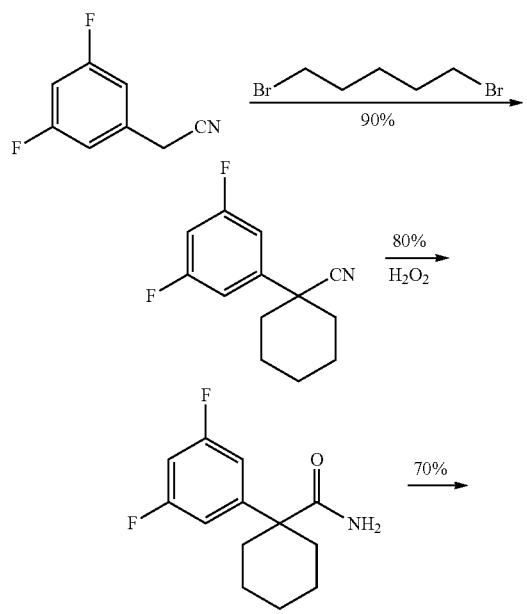

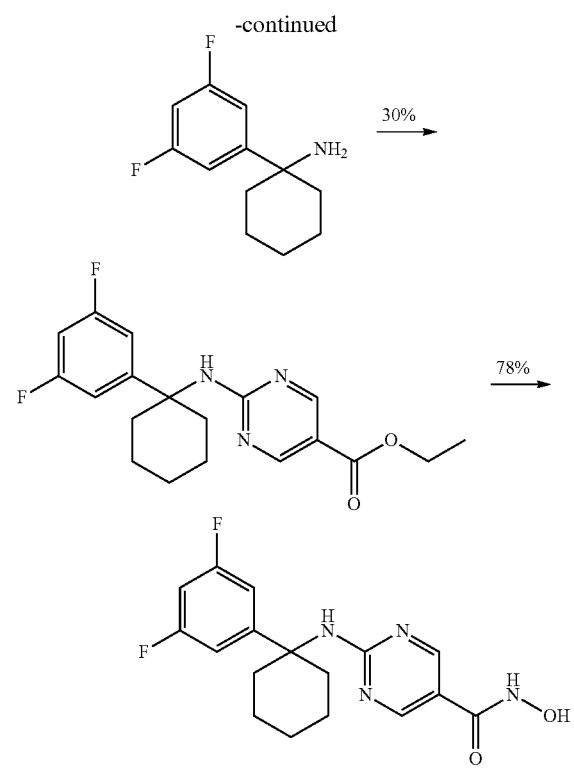

Synthesis of 1-(3, 5-difluorophenyl)cyclohexanecarbonitrile: To a solution of 2-(3,5-difluorophenyl)acetonitrile (10 g, 65 mmol) in dry DMF (200 ml) was added 1,5-dibromopentane (15 g, 65 mmol), NaH (5.7 g, 2.2 eq.) dropwise with cooling by an ice bath. After addition, the resulting mixture was vigorously stirred overnight at 50° C. The suspension was quenched by ice water carefully, extracted with ethyl acetate (3×1800 ml). The combined organic solution was concentrate to afford the crude product, which was purified by flash column chromatography to give 1-(3, 5-difluorophenyl)cyclohexanecarbonitrile as a white solid (12.9 g, 90%).

Synthesis of 1-(3, 5-difluorophenyl)cyclohexanecarboxamide: To a solution of 1-(3,5-difluorophenyl)cyclohexanecarbonitrile (12.9 g, 58 mmol) in DMSO (100 ml) was added $K_2CO_3$ (116 mmol) and $H_2O_2$ (35 ml) dropwise. The mixture was heated at 50-60° C. overnight. At this time, the resulting mixture was carefully diluted with water. The precipitate was collected and washed with water (500 ml) to afford 1-(3, 5-difluorophenyl)cyclohexanecarboxamide as white solid (11.1 g, 80%).

Synthesis of 1-(3, 5-difluorophenyl)cyclohexanamine: To a solution of 1-(3,5-difluorophenyl)cyclohexanecarboxamide (11.1 g, 46 mmol) in t-BuOH (100 ml) was added NaClO (50 ml, 2.8 eq), then 3N NaOH (40 ml, 2.8 eq) was added at 0° C. and the reaction was stirred overnight at r.t. The resulting mixture was extracted with EA (2×120 ml), and the combined organic layers were washed with brine and dried to afford the crude product. Further purification by treatment with HCl salt yielded a white powder (6.8 g, 70%).

Synthesis of ethyl 2-(1-(3, 5-difluorophenyl)cyclohexylamino)pyrimidine-5-carboxylate: To a solution of 1-(3,5-difluorophenyl)cyclohexanamine hydrochloride (6.8 g 27 mmol) in dioxane (60 ml) was added ethyl 2-chloropyrimidine-5-carboxylate (5.0 g, 1.0 eq) and DIPEA (7.0 g, 2.0 eq). The mixture was heated overnight at 110-120° C. The resulting mixture was directly purified on a silica gel column to afford the coupled product as white solid (2.9 g, 30%)

Synthesis of Compound 001: To a solution of ethyl 2-(1-(3,5-difluorophenyl)cyclohexylamino)pyrimidine-5-carboxylate (2.9 g, 8 mmol) in MeOH/DCM (60 ml, 1:1) was added 50% NH$_2$OH in water (10 ml, excess), which was followed by addition of sat. NaOH in MeOH (10 ml, excess) at 0° C. The resulting reaction mixture was stirred for 3-4 hours. After completion, the resulting mixture was concentrated and acidified with 2N HCl to a pH of ~4-5. The precipitate was collected and washed by water (50 ml) to remove the NH$_2$OH and dried to afford Compound 001 as a white powder (2.2 g, 78%). $^1$H NMR (500 MHz, DMSO) δ 10.89 (s, 1H), 9.01 (s, 1H), 8.62 (s, 1H), 8.38 (d, J=18.3 Hz, 1H), 7.91 (s, 1H), 7.18-6.89 (m, 3H), 2.53 (s, 2H), 1.64 (ddd, J=53.7, 29.1, 16.6 Hz, 7H), 1.38-1.16 (m, 1H). LCMS: m/z=349 (M+H)$^+$.

Example 2

Synthesis of Compound 002

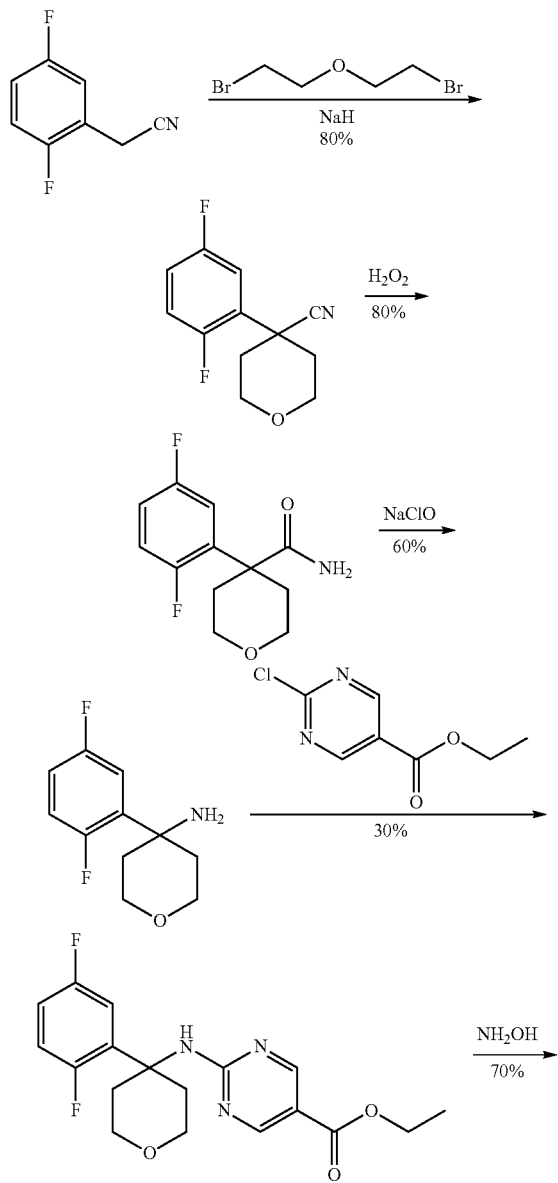

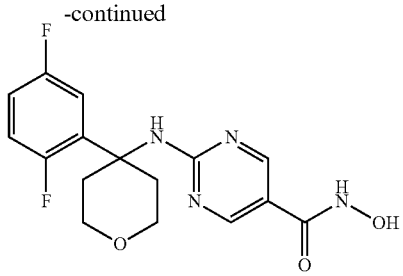

Synthesis of 4-(2,5-difluorophenyl)tetrahydro-2H-pyran-4-carbonitrile: To a solution of 2-(2,5-difluorophenyl)acetonitrile (10 g, 65 mmol) in dry DMF (200 ml) was added 1-bromo-2-(2-bromoethoxy)ethane (15 g, 65 mmol), and NaH (5.7 g, 2.2 eq) was added dropwise while cooled by an ice bath. After addition, the resulting mixture was vigorously stirred overnight at 50° C. The suspension was quenched by ice water carefully, extracted with ethyl acetate (3×200 ml). The combined organic layers were concentrated to afford the crude product, which was purified by flash column chromatography to give 4-(2,5-difluorophenyl)tetrahydro-2H-pyran-4-carbonitrile as a pale solid (11.6 g, 80%).

Synthesis of 4-(2, 5-difluorophenyl)tetrahydro-2H-pyran-4-carboxamide: To a solution of 4-(2, 5-difluorophenyl)tetrahydro-2H-pyran-4-carbonitrile (11.6 g, 52 mmol) in DMSO (100 ml) was added K$_2$CO$_3$ (104 mmol) and H$_2$O$_2$ (30 ml) dropwise. The mixture was heated at 50-60° C. overnight. After completion, the resulting mixture was carefully diluted with water. The precipitate was collected and washed with water (500 ml) to afford 4-(2, 5-difluorophenyl)tetrahydro-2H-pyran-4-carboxamide as a white solid (10.1 g, 80%).

Synthesis of 4-(2, 5-difluorophenyl)tetrahydro-2H-pyran-4-amine: To a solution of 4-(2, 5-difluorophenyl)tetrahydro-2H-pyran-4-carboxamide (10.1 g, 42 mmol) in t-BuOH (100 ml) was added NaClO (49 ml, 2.8 eq), then 3N NaOH (38 ml, 2.8 eq) was added at 0° C. and the reaction was stirred overnight at r.t. The resulting mixture was extracted with EA (2×100 ml), and the combined organic solution was washed with brine and dried to afford the crude product. The crude product was further purified by treatment with HCl salt to yield a white powder (5.3 g, 60%).

Synthesis of ethyl 2-(4-(2,5-difluorophenyl)tetrahydro-2H-pyran-4-ylamino)pyrimidine-5-carboxylate: To a solution of 4-(2,5-difluorophenyl)tetrahydro-2H-pyran-4-amine hydrochloride (5.3 g, 21 mmol) in dioxane (50 ml) was added ethyl 2-chloropyrimidine-5-carboxylate (3.9 g, 1.0 eq) and DIPEA (5.4 g, 2.0 eq). The mixture was heated overnight at 110-120° C. The resulting mixture was directly purified on a silica gel column to afford the coupled product as white solid (2.7 g, 30%).

Synthesis of Compound 002: To a solution of ethyl 2-(4-(2,5-difluorophenyl)tetrahydro-2H-pyran-4-ylamino) pyrimidine-5-carboxylate (2.7 g, 7 mmol) in MeOH/DCM (60 ml, 1:1) was added 50% NH$_2$OH in water (10 ml, excess). Then, sat. NaOH in MeOH (10 ml, excess) was added at 0° C. and the reaction was stirred for 3-4 hours. After completion, the resulting mixture was concentrated and acidified with 2N HCl to a PH of ~4-5. The precipitate was collected and washed with water (50 ml) to remove the NH$_2$OH, and dried to afford Compound 002 as white powder (1.8 g, 70%). $^1$H NMR (500 MHz, DMSO) δ 10.94 (s, 1H), 9.00 (s, 1H), 8.58 (s, 1H), 8.45-8.30 (m, 1H), 8.26 (s, 1H), 7.24-7.16 (m, 1H), 7.15-7.04 (m, 2H), 3.72 (d, J=7.7 Hz, 4H), 3.33 (s, 2H), 2.60 (d, J=13.1 Hz, 2H), 2.16-2.03 (m, 2H). LCMS: m/z=351 (M+H)$^+$.

Example 3

Synthesis of Compound 003

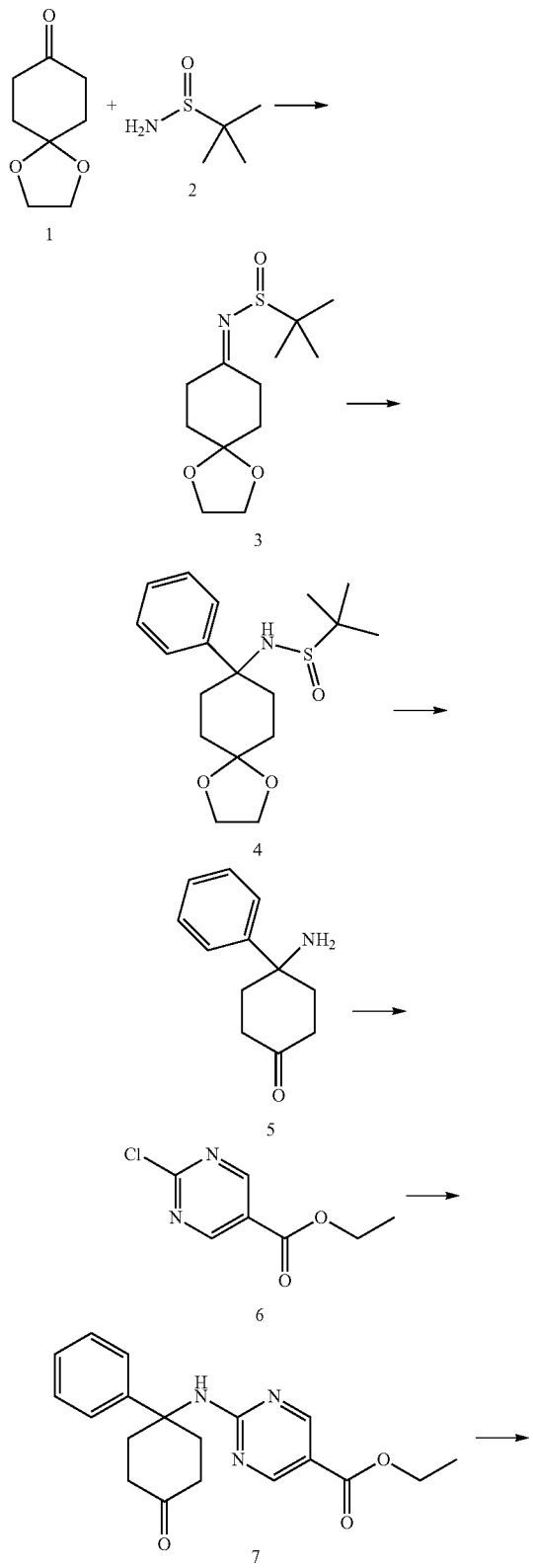

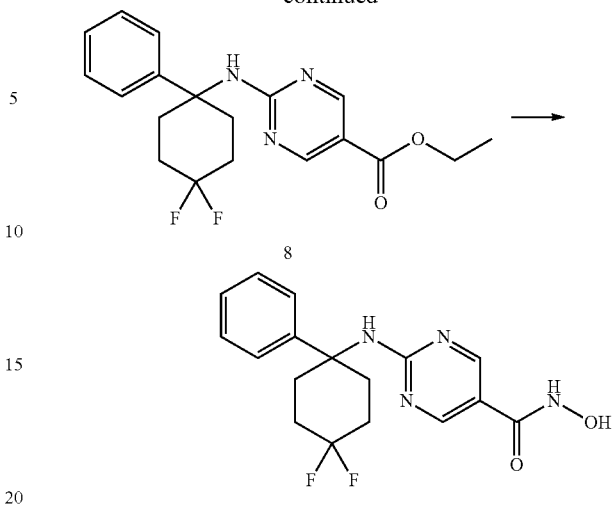

Step 1: To a solution of 1 (2.00 g, 12.81 mmol) and 2 (1.552 g, 12.81 mmol) in THF (20 mL) was added Ti(OEt)$_4$ (5.4 mL, 25.56 mmol). The mixture was stirred at r.t. for 16 hrs and then poured into saturated NaHCO$_3$ solution at 0° C. The resulting precipitate was filtered off. The resulting filtrate was extracted with EA. The combined EA layers were concentrated in vacuo and the residue was purified by silica gel chromatography (PE/EA=4/1, 2/1) to afford 3 as a white solid (2.61 g, yield: 75%).

Step 2: To a flask containing 3 (1.00 g, 3.86 mmol) was added a solution of PhMgBr (1M in THF, 10 mL) at 0° C. It was stirred at 0° C. to rt until a complete reaction. Saturated NH$_4$Cl solution was added to adjust pH 6-7. The resulting mixture was extracted with EA. The combined EA layers were concentrated in vacuo and the residue was purified by silica gel chromatography (PE/EA=5/1, 2/1, 1.5/1) to afford 4 as a white solid (823 mg, yield: 60%).

Step 3: A mixture of compound 4 (8.3 mg, 2.38 mmol) in HCl (2M in water, 20 mL) and THF (20 mL) was stirred at 50° C. for 16 hrs. A solution of NaOH was added to the mixture to adjust pH 7-8. THF was removed in vacuo and the aqueous phase was extracted with EA. The combined EA layers were concentrated in vacuo and the residue was dissolved in EA. HCl (4 M, 1 mL) was added. The resulting white solid was collected by filtration to afford desired product 5 (395 mg, yield: 57%).

Step 4: A mixture of compound 5 (350 mg, 1.55 mmol), 6 (376 mg, 2.02 mol), and DIPEA (1.07 mL, 6.47 mmol) in NMP (4 mL) was stirred at 130° C. for 5 hrs. The mixture was added water (20 mL), extracted with EA (25 mL×2). The organic layer was concentrated to get a residue, which was purified by silica gel chromatography (PE/EA=4/1) to afford 7 (178 mg, yield: 34%).

Step 5: To a solution of compound 7 (168 mg, 0.50 mmol) in DCM (30 mL) was added DAST (302 μL, 2.47 mmol) at 0° C. It was stirred at rt for 3 hrs and 35° C. for 2 hrs. The reaction mixture was quenched with saturated NaHCO$_3$ (5 mL), and extracted with EtOAc (2×5 mL). The organic extracts were concentrated in vacuo. The residue was purified by pre-TLC to give 8 (74 mg, yield: 42%).

Step 6: NH$_2$OH (50% in water, 3.9 mL) was added to a flask containing 8 (74 mg, 0.20 mmol) at 0° C. Then saturated NaOH solution in MeOH (3.9 ml) was added at 0° C. DCM (3.9 mL) was added to aid substrate to dissolve. The mixture was heated at 25° C. for 18 hrs. Con. HCl was added to adjust pH to 7. It was concentrated in vacuo and the residue was purified by pre-HPLC to afford Compound 003 (27 mg, yield: 38%) as a white solid. ¹H NMR (500 MHz, DMSO) δ 10.96 (s, 1H), 9.00 (s, 1H), 8.63 (s, 1H), 8.35 (s, 1H), 8.29 (s, 1H), 7.39 (d, J=7.6 Hz, 2H), 7.28 (t, J=7.7 Hz, 2H), 7.17 (t, J=7.3 Hz, 1H), 2.73 (s, 2H), 2.23-1.88 (m, 6H). LCMS: m/z=349 (M+H)⁺.

Example 4

Synthesis of Compound 004

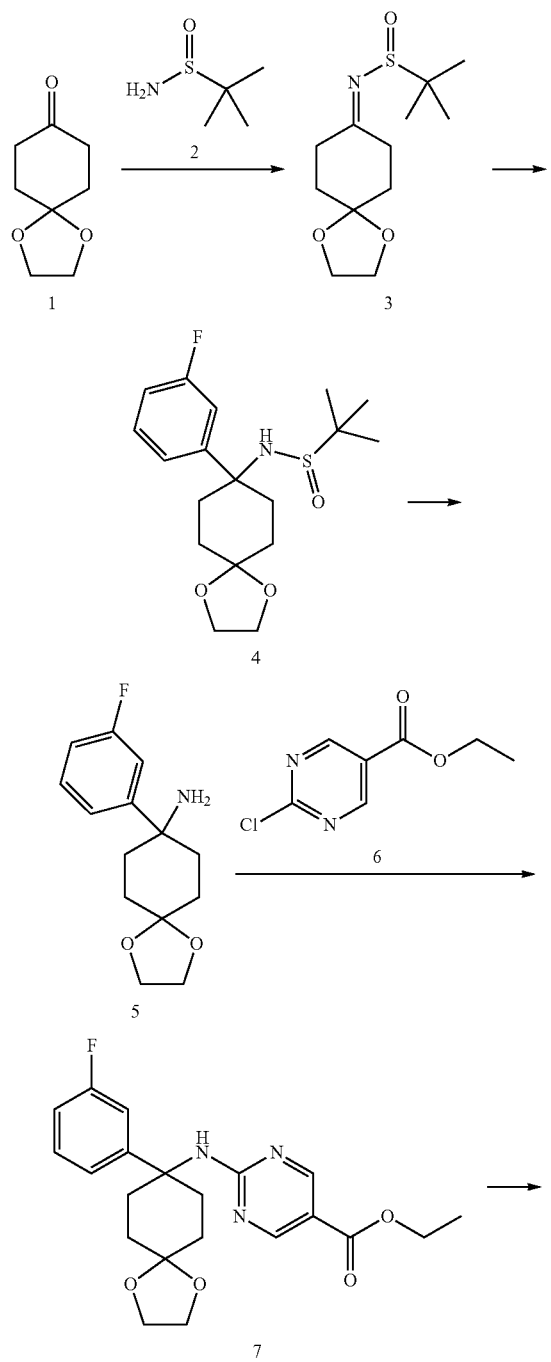

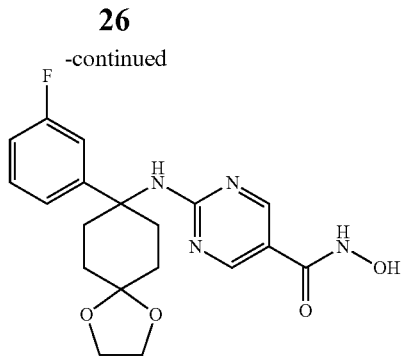

Step 1: To a solution of 1 (2.40 g, mmol) and 2 (1.552 g, 12.81 mmol) in THF (2 mL) was added Ti(OEt)4 (10 mL). The mixture was stirred at 55° C. for 16 hrs. Then it was poured into saturated NaHCO₃ and EA at 0° C. The resulting precipitate was filtered and the filtrate was extracted with EA. The combined EA layers were dried and filtered through silica gel (10~15 cm) and concentrated in vacuo to afford 3 as a yellow solid (2.8 g, yield: 85%) to be used in Step 2 without further purification.

Step 2: To a flask containing 3 (2.6 g, 10 mmol) was added a solution of PhMgBr (1 M in THF, 30 mL) at −78° C. under a N₂ atmosphere. The mixture was stirred at 0° C. and allowed to warm to r.t. overnight. TLC (EA: PE=1:1) and LCMS was used to monitor reaction completion. The reaction mixture was concentrated at 25° C. to yield a residue, sat. NH4Cl solution was added at −78° C. to adjust the pH to 6~7, and the mixture was stirred at 0° C. for 1 h. The resulting mixture was extracted with EA and the combined EA layers were concentrated in vacuo. The residue was purified by silica gel column to yield 4 as a light yellow solid (500 mg, yield: 20%).

Step 3: A mixture of compound 4 (500 mg, 1.4 mmol) and TsOH (48 mg, 0.28 mmol) in THF (5 mL) was stirred at r.t. for 16 hrs. A solution of NaHCO₃ was added to the mixture to adjust the pH to 7~8. THF was removed in vacuo and the aqueous phase was extracted with EA. The combined EA layers were concentrated to afford desired product 5 (300 mg, yield: 85%).

Step 4: A mixture of compound 5 (300 mg, 1.19 mmol), 6 (333 mg, 1.78 mol), and DIPEA (1.07 mL, 6.47 mmol) in DMSO (4 mL) was stirred at 100° C. overnight. To the mixture was added water (20 mL), followed by extraction with EA (25 mL×2). The organic layer was concentrated to give a residue, which was purified by silica gel chromatography to afford 7 (143 mg, yield: 30%).

Step 5: NH₂OH (50% in water, 3.9 mL) was added to a solution containing 7 (100 mg, 0.24 mmol) at 0° C. Then saturated NaOH solution in MeOH (3.9 mL) was added at 0° C. DCM (3.9 mL) was added to help dissolve the substrate. The mixture was stirred for 3 h at 0° C. Conc. HCl was added to adjust the pH to 7. The mixture was concentrated in vacuo and the residue was purified by pre-HPLC to afford Compound 004 (10 mg, yield: 10%) as a white solid. ¹H NMR (400 MHz, DMSO) δ 10.81 (s, 1H), 8.98 (s, 1H), 8.48 (d, J=94.6 Hz, 2H), 8.14 (s, 1H), 7.31 (dd, J=14.3, 7.9 Hz, 1H), 7.22 (d, J=8.0 Hz, 1H), 7.12 (d, J=11.1 Hz, 1H), 6.98 (dd, J=11.5, 5.1 Hz, 1H), 3.88 (s, 4H), 2.58 (s, 2H), 1.94 (t, J=17.9 Hz, 2H), 1.80 (t, J=12.2 Hz, 2H), 1.58 (d, J=11.9 Hz, 2H). LCMS: 1.413 min, m/z=389.2 (M+H)⁺.

Example 5

HDAC Enzyme Assays

Compounds for testing were diluted in DMSO to 50 fold the final concentration and a ten point three fold dilution series was made. The compounds were diluted in assay buffer (50 mM HEPES, pH 7.4, 100 mM KCl, 0.001% Tween-20, 0.05% BSA, 20 µM TCEP) to 6 fold their final concentration. The HDAC enzymes (purchased from BPS Biosciences) were diluted to 1.5 fold their final concentration in assay buffer. The tripeptide substrate and trypsin at 0.05 µM final concentration were diluted in assay buffer at 6 fold their final concentration. The final enzyme concentrations used in these assays were 3.3 ng/ml (HDAC1), 0.2 ng/ml (HDAC2), 0.08 ng/ml (HDAC3) and 2 ng/ml (HDAC6). The final substrate concentrations used were 16 µM (HDAC1), 10 µM (HDAC2), 17 µM (HDAC3) and 14 µM (HDAC6).

Five µl of compounds and 20 µl of enzyme were added to wells of a black, opaque 384 well plate in duplicate. Enzyme and compound were incubated together at room temperature for 10 minutes. Five µl of substrate was added to each well, the plate was shaken for 60 seconds and placed into a Victor 2 microtiter plate reader. The development of fluorescence was monitored for 60 min and the linear rate of the reaction was calculated. The $IC_{50}$ was determined using Graph Pad Prism by a four parameter curve fit. The $IC_{50}$ values (nM) obtained for several of the compounds of this invention are found in Table 2, below.

TABLE 2

| Compound ID | Structure | HDAC1 | HDAC2 | HDAC3 | HDAC6 |
| --- | --- | --- | --- | --- | --- |
| 001 | 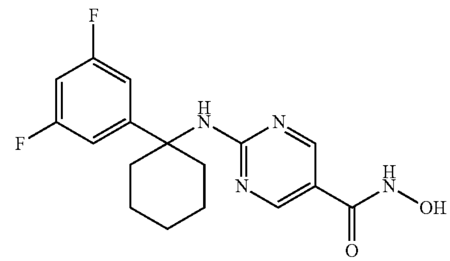 [SMILES: O=C(NO)c1cnc(NC2(c3cc(F)cc(F)c3)CCCCC2)nc1] | 1041 | 870 | 6200 | 2.9 |
| 002 | 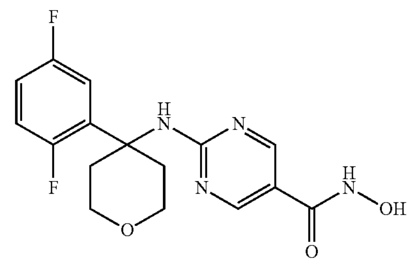 [SMILES: O=C(NO)c1cnc(NC2(c3cc(F)ccc3F)CCOCC2)nc1] | 117 | 108 | 671 | 2.4 |
| 003 | 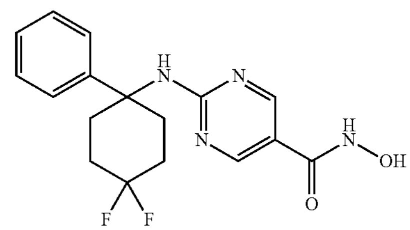 [SMILES: O=C(NO)c1cnc(NC2(c3ccccc3)CCC(F)(F)CC2)nc1] | 961 | 982 | 4380 | 3.7 |
| 004 | 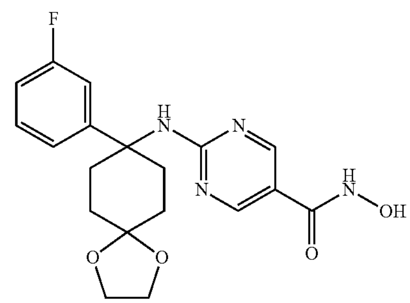 [SMILES: O=C(NO)c1cnc(NC2(c3cccc(F)c3)CCC3(CC2)OCCO3)nc1] | 703 | 833 | 1821 | 3.9 |

Example 6

Rat Pharmacokinetic Studies

Male SD rats were fasted overnight. Compounds of the invention as well as two previously known HDAC6 inhibitors, Compounds A and B were dissolved in dimethyl acetamide at 10 times the final concentration, then Solutol HS 15 (BASF) was added to a final concentration of 10%. Finally 80% saline was added and vortexed to achieve a clear solution. For the IV dosing three animals were injected via the foot dorsal vein with 1 mg/kg compound. For the PO dosing 5 mg/kg of compound was delivered by oral gavage. Blood was collected via the tail vein into K2EDTA tubes at 5 minutes, 15 minutes, 30 minutes, 1 hour, 2 hours, 4 hours, 8 hours and 24 hours after dosing. The blood was centrifuged at 2000 g for 5 minutes at 4° C. to obtain plasma. The plasma was extracted with acetonitrile and the level of compound was analyzed by LC/MS/MS. The level of compound in plasma was calculated from a standard curve in rat plasma. The IV clearance and area under the curve were calculated using WinNonLin software. The dose adjusted area under the curve for the IV and oral dosing were used to calculate the oral bioavailability. A summary of results is presented in Table 3. Compounds A and B, previously known HDAC6 inhibitors, are shown below (See, e.g., U.S. Pat. No. 8,614,223):

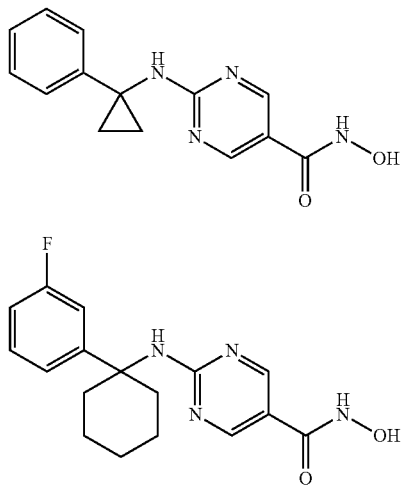

Compound A

Compound B

Example 7

Mouse Pharmacokinetic Studies

Male C57BL/6 mice were fasted overnight. Compounds of the invention as well as two previously known HDAC6 inhibitors, Compounds A and B, were dissolved in dimethyl acetamide at 10 times the final concentration, then Solutol HS 15 (BASF) was added to a final concentration of 10%. Finally 80% saline was added and vortexed to achieve a clear solution. Fifteen animals were injected via the tail vein with 1 mg/kg compound. Blood was collected by retro-orbital bleed at 5 minutes, 15 minutes, 30 minutes, 1 hour, 2 hours, 4 hours, 8 hours and 24 hours after dosing. At 5 minutes, 30 minutes, 1 hour and 4 hours after dosing three animals per time point were sacrificed and brains were removed. The blood was centrifuged at 2000 g for 5 minutes at 4° C. to obtain plasma. Brain samples were homogenized in PBS. The plasma and brain homogenate were extracted with acetonitrile and the level of compound was analyzed by LC/MS/MS. The level of compound in plasma was calculated from a standard curve in rat plasma and the level in brain was calculated from a standard curve in brain homogenate. The area under the curve in plasma and brain were calculated using WinNonLin software. The brain to plasma ratio was determined using the area under the curve values for the two compartments. A summary of the results is presented in Table 3.

TABLE 3

| Compound | Rat IV Clearance (L/hr/kg) | Rat Oral Bioavailability (%) | Mouse plasma/brain ratio |
|---|---|---|---|
| Compound A | 6.0 | 16.5 | 1.23 |
| Compound B | 2.3 | 7.9 | 1.28 |
| Compound 001 | 5.5 | 11.1 | 2.55 |
| Compound 002 | 5.6 | 18.4 | 0.45 |
| Compound 003 | 3.7 | 41.5 | 0.67 |

Inhibition of HDAC1, 2 and 3 have been associated with toxicity, such as thrombocytopenia, neutropenia, anemia, and fatigue. A compound with a higher selectivity for HDAC6 over HDACs 1, 2 and 3 would therefore be expected to have a larger therapeutic window.

For use in therapy, compounds must have a low IV clearance rate (to maintain biologically active concentrations in plasma and tissues for a prolonged time), a high oral bioavailability (to allow consistent delivery of compound by the oral route) and a high blood brain barrier penetration (to allow compound to reach the relevant target in the brain).

Compound 003 has the most favorable combination of biochemical and pharmacokinetic properties. The compound is among the most selective HDAC6 inhibitors yet described. Compound 003 has the added advantage of being highly orally bioavailable with a low IV clearance and good blood brain barrier penetration.

Example 8

Cell-Based Assay of Compound Activity

Figure 2:
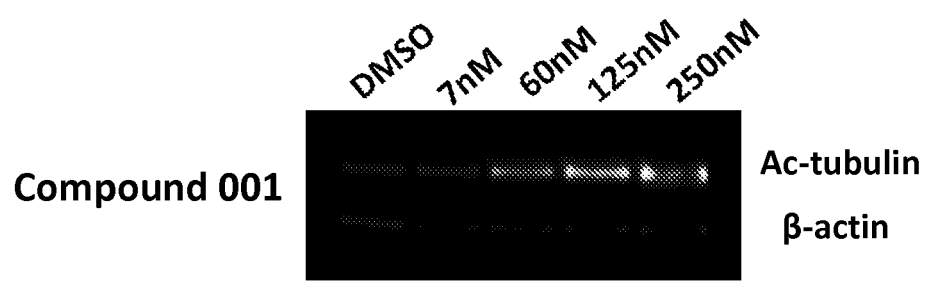
FIG. 2 shows tubulin acetylation of SH-SY5Y neuroblastoma cells after 5 h of treatment with various concentrations of Compound 001.
Figure 3:
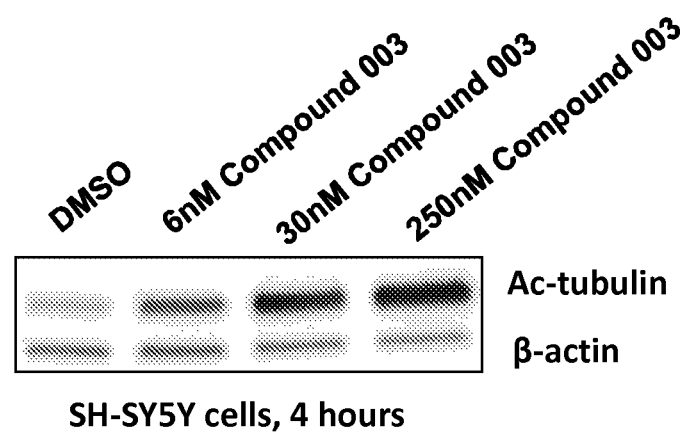
FIG. 3 shows tubulin acetylation of SH-SY5Y neuroblastoma cells after 4 h of treatment with various concentrations of Compound 003.

A study was conducted to determine the concentration of compound that inhibits HDAC6 within cells. For this study we used a human neuroblastoma cell line, SH-SY5Y, as a substitute for neuronal cells. The cells were plated in a 12 well plate and incubated for two days to achieve approximately 75% confluence. The media was changed and the cells were treated with varying concentrations of HDAC inhibitors as described in the figures. After the incubation (either 4 or 5 hours, as described in the figures) the cells were washed twice with PBS and lysed in 0.1% Triton X-100/HEPES buffer containing protease inhibitors. The lysates were incubated for 10 minutes on ice then centrifuged at 14,000×g for 10 minutes to remove nuclei. The nuclei were extracted with a histone extraction kit (Epigentek) to obtain a histone fraction (FIG. 1). The cytoplasmic lysate (FIGS. 1, 2, and 3) and the histone extract (FIG. 1) were subjected to western blot for tubulin acetylation, histone acetylation, or loading control proteins as described in the figures. Tubulin acetylation was detected with the monoclonal antibody 6-11b-1 (Sigma). Histone acetylation was detected with the rabbit antibody C5B11 (Cell Signaling Technology).

Example 9

Taxol Induced Neuropathic Pain Study in Rats

A study was conducted to confirm findings that HDAC6 inhibition reverses pain in the taxol induced neuropathic pain model in rats by using a more selective HDAC6 inhibitor, Compound 003. This study included a histology endpoint in addition to the von Frey testing for paw sensitivity.

Methods:

Taxol Treatment:

Neuropathic pain is induced by a 0.5 ml/kg injection of Taxol (2 mg/kg) administered IP on days 0-12. The development of neuropathic pain is confirmed by measuring mechanical allodynia (Von Frey test) on study day 13.

Pain Response Evaluation (Von Frey Testing):

Allodynic response to tactile stimulation is assessed using the Von Frey apparatus (Touch Test®).

The rat will be placed in an enclosure and positioned on a metal mesh surface, but allowed to move freely. The rats' cabins are covered with red cellophane to diminish environmental disturbances. The test begins after a cessation of exploratory behavior. The set of Von Frey monofilaments provide an approximate logarithmic scale of actual force and a linear scale of perceived intensity.

The operating principle: when the tip of a fiber of given length and diameter is pressed against the skin at right angles, the force of application increases as long as the researcher continues to advance the probe until the fiber bends. After the fiber bends, the probe continues to advance, causing the fiber to bend more, but without additional force being applied. Rodents exhibit a paw withdrawal reflex when the paw is unexpectedly touched. The Touch Test™ Sensory Evaluator can be used on the plantar surfaces of the rat's foot. The animal indicates sensation by pulling back its paw. The minimal force needed to elevate the withdrawal reflex is considered/designated as the value of reference. In order to achieve paw withdrawal, the pressure applied is sometimes greater than 60 g, often requiring the researcher to apply enough pressure with the Von Frey filament to actually lift the paw of the naive animal. Decreases in force needed to induce withdrawal are indicative of allodynia, as the force applied is a non-painful stimulus under normal conditions.

| Group No. | Group Size | Test Item | Dose | Volume | Route | Administration Regime |
|---|---|---|---|---|---|---|
| 1 | N = 15 | Vehicle | N/A | N/A | PO | Twice a day (b.i.d) from study day 7 through day 12. On days 12-15 twice a day (b.i.d) 2 hours prior to Von Frey testing.** |
| 2 | N = 15 | Gabapentin | 150 mg/kg | 3 ml/kg | IP | Once, 2 hours prior to testing on study days, 13, 14 and 15 (AM dosing)*. |
| 4 | N = 10 | Compound 003 | 1 mg/kg | 5 ml/kg | PO | Twice a day (b.i.d) from study day 7 through day 12. |
| 5 | N = 10 | Compound 003 | 3 mg/kg | 5 ml/kg | PO | On days 12-15 twice a day (b.i.d) 2 hours prior |
| 6 | N = 10 | Compound 003 | 10 mg/kg | 5 ml/kg | PO | to Von Frey testing.** |

*Note:
Saline was second daily dosing (PM) for animals treated with gabapentin (group2)

**Note:
Vehicle and test items were dosed once on study termination (day 15)

Summary:

Following injection of taxol, animals administered with Vehicle experienced pain as was assessed by the reduction in withdrawal force that was noticed on study day 13 (15.10±1.04 g force). This low withdrawal force was also observed on the last day of the study (study day 15: 13.80±1.27 g; $p<0.05$ vs. baseline).

Treatment with gabapentin at a dose of 150 mg/kg (Group 2) significantly reversed nociception vs. Vehicle at 2 hours post dosing: on study day 13: 58.30±1.70 g, on study day 14: 60.00±0.00 g and on study day 15: 58.30±1.70 g ($p<0.05$ vs. vehicle).

Figure 4:
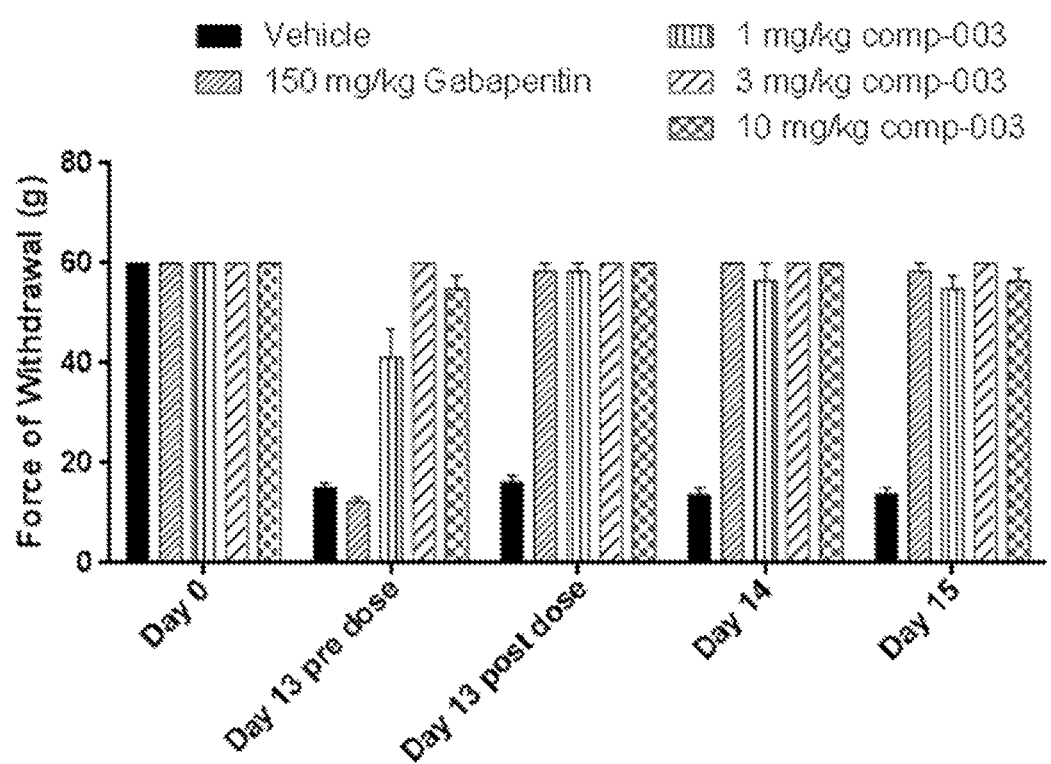
FIG. 4 shows the results of Von Frey Testing in which it was found that Compound 003 reduced tactile allodynia in taxol treated rats.

Treatment with Compound 003 completely reversed nociception. No dose response was found following treatment with Compound 003 as even the lowest dose tested in this study (1 mg/kg) was highly active in reversing nociception (study day 15: 58.30±1.70 g). On study day 13 pre-dosing the mean group withdrawal force was 41.10±5.88 g, significantly higher than the withdrawal force measured following treatment with the vehicle (15.10±1.04 g) suggesting a relatively long duration of test item's activity as the last dose was carried out the day before (day 12, b.i.d dosing). The results of the Von Frey Test are shown in FIG. 4.

We claim:

1. A compound selected from the following:

or pharmaceutically acceptable salts thereof.

2. The compound of claim 1, which is

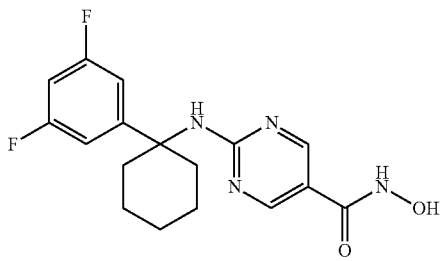 [SMILES: O=C(NO)c1cnc(NC2(c3cc(F)cc(F)c3)CCCCC2)nc1]

or a pharmaceutically acceptable salt thereof.

3. The compound of claim 1, which is

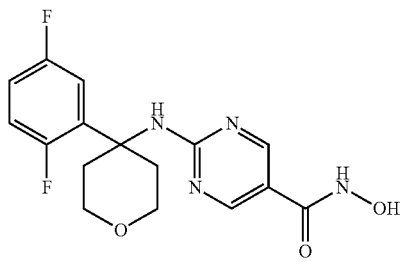 [SMILES: O=C(NO)c1cnc(NC2(c3cc(F)ccc3F)CCOCC2)nc1]

or a pharmaceutically acceptable salt thereof.

4. A pharmaceutical composition comprising a compound of claim 1, or a pharmaceutically acceptable salt thereof, together with a pharmaceutically acceptable carrier.

5. A method of treating a peripheral neuropathy in a subject in need thereof comprising administering to the subject a therapeutically effective amount of a compound of claim 1, to thereby treat the peripheral neuropathy.

6. The method of claim 5, wherein the peripheral neuropathy is Charcot-Marie Tooth Disease.

7. The method of claim 5, wherein the peripheral neuropathy is chemotherapy induced peripheral neuropathy.

8. The method of claim 7, wherein the chemotherapy induced peripheral neuropathy is taxol induced peripheral neuropathy or vincristine induced peripheral neuropathy.

9. The method of claim 5, wherein the subject is a human.

* * * * *